United States Patent [19]

Takechi et al.

[11] Patent Number: 5,536,735

[45] Date of Patent: Jul. 16, 1996

[54] PHARMACEUTICAL COMPOSITION

[75] Inventors: Nobuyuki Takechi, Ikeda; Akihiro Nagai, Toyono-gun; Naoru Hamaguchi, Ibaraki, all of Japan

[73] Assignee: Takeda Chemical Industries, Ltd., Osaka, Japan

[21] Appl. No.: 322,485

[22] Filed: Oct. 14, 1994

[30] Foreign Application Priority Data

Oct. 15, 1993 [JP] Japan ................... 5-258655

[51] Int. Cl.⁶ ..................... A61K 31/44
[52] U.S. Cl. .............. 514/338; 514/355; 514/563; 514/357
[58] Field of Search ................. 514/338, 355, 514/563, 357

[56] References Cited

U.S. PATENT DOCUMENTS

| | | | |
|---|---|---|---|
| 4,628,098 | 12/1986 | Nohara et al. | 546/27 |
| 4,954,512 | 9/1990 | Oguro et al. | 514/352 |
| 5,223,515 | 6/1993 | Mikura et al. | 514/322 |

FOREIGN PATENT DOCUMENTS

| | | | |
|---|---|---|---|
| 0055179 | 6/1982 | European Pat. Off. | C07D 213/70 |
| 0124495 | 11/1984 | European Pat. Off. | C07D 401/12 |

OTHER PUBLICATIONS

Howden et al 109CA:85750m 1988.
Am. J. Hosp. Pharm., 46, (1989).

*Primary Examiner*—Russell Travers
*Attorney, Agent, or Firm*—Foley & Lardner

[57] ABSTRACT

This invention comprises a pharmaceutical composition comprising a benzimidazole compound having antiulcer activity and a water-soluble carboxylic acid amide. According to this invention, a water-insoluble benzimidazole compound having antiulcer activity can be solubilized and a stable pharmaceutical composition can be provided. The solid pharmaceutical composition of this invention can be extemporaneously dissolved in sterile distilled water or an infusion (e.g. physiological saline, glucose infusion, etc.) and put to use as an injection with great convenience.

10 Claims, No Drawings

PHARMACEUTICAL COMPOSITION

FIELD OF THE INVENTION

This invention relates to a pharmaceutical composition comprising a benzimidazole compound having antiulcer activity and a water-soluble carboxylic acid amide. The pharmaceutical composition of this invention finds application as an antiulcer drug.

BACKGROUND OF THE INVENTION

Because of their gastric acid antisecretory and gastric mucosa-protective activities, certain benzimidazole compounds are gathering attention as therapeutic agents for ulcer and/or prophylactic agents for relapse of ulcer.

To provide an intravenous dosage composition of the above compound, it has been proposed to subject a solution of omeprazole sodium in sterile water to filtration and lyophilization and reconstituting the lyophilizate extemporaneously in a filtration-sterilized mixture of injection-grade polyethylene glycol 400, sodium dihydrogen phosphate and sterile water (EP-A-124495) but the stability of the active substance in the composition is not fully satisfactory.

An injectable solution containing (a) 2-[(pyridyl)methylsulfinyl]benzimidazole compounds which are useful as an anti-ulcer agent and (b) at least one solvent selected from the group consisting of ethanol, propylene glycol and polyethylene glycol was known (U.S. Pat. No. 5,223,515), but it has not been reported that nicotinamide is used with the benzimidazole compounds for injectable solution.

OBJECTS OF THE INVENTION

The main object of the present invention is to provide a highly stabilized pharmaceutical composition.

This object as well as other objects and advantages of the present invention will become apparent to those skilled in the art from the following description.

SUMMARY OF THE INVENTION

The inventors of this invention explored into the above problems for years and discovered that the benzimidazole compound having antiulcer activity is highly soluble in an aqueous solution of an amide, such as nicotinamide or benzamide, and remains quite stable in such solution and that a composition obtainable by dissolving the compound in such an aqueous amide solution and lyophilizing or spray-drying the solution shows no coloration with time and offers a long shelf-life as well as good water-reconstitutability. These findings were followed by their further research, which has brought this invention into being.

According to this invention, there is provided:

1) A pharmaceutical composition which comprises a benzimidazole compound having antiulcer activity and a water-soluble carboxylic acid amide, 2) The composition according to 1) above, wherein the benzimidazole compound is represented by the formula:

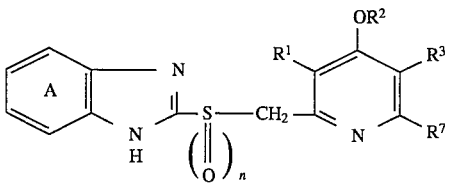

wherein ring A may optionally be substituted, $R^1$, $R^3$ and $R^7$ are, the same or different, hydrogen, an alkyl or alkoxy group, $R^2$ is a hydrocarbon group which may optionally be substituted, and n is 0 or 1, or a salt thereof, 3) The composition according 2) above, wherein $R^1$ and $R^3$ are, the same or different, hydrogen, an alkyl or alkoxy group, $R^2$ is a $C_{1-4}$ alkyl group which may optionally be substituted by (1) halogen or (2) a $C_{1-4}$ alkoxy group, and $R^7$ is a hydrogen atom, 4) The composition according to 1) above, wherein the benzimidazole compound is 2-[2-[3-methyl-4-(2,2,2-trifluoroethoxy)pyridyl]methylsulfinyl]benzimidazole, 5) The composition according to 1) above, wherein the water-soluble carboxylic acid amide is a compound represented by the formula:

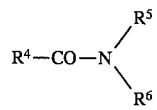

wherein $R^4$ is hydrogen, amino, an alkyl group which may optionally be substituted, an aryl group which may optionally be substituted or a N-containing heterocyclic group which may optionally be substituted, $R^5$ and $R^6$ are, the same or different, hydrogen or an alkyl group, 6) The composition according to 5) above, wherein $R^4$ is a N-containing heterocyclic group which may optionally be substituted, $R^5$ and $R^6$ are, the same or different, hydrogen or an alkyl group, 7) The composition according to 5) above, wherein the water-soluble carboxylic acid amide is nicotinamide, 8) The composition according to 1) above, which further comprises at least one sugar, 9) The composition according to 8) above, wherein the sugar is a sugar alcohol, 10) The composition according to 1) above, which is a lyophilizate, 11) The composition according to 1) above, which is an aqueous solution, 12) The composition according to 11) above, wherein the aqueous solution is an injectable solution, and 13) The composition according to 10) above, which is produced by lyophilizing an alkaline aqueous solution comprising a benzimidazole compound having antiulcer activity and a water-soluble carboxylic acid amide.

DETAILED DESCRIPTION OF THE INVENTION

The benzimidazole compound having antiulcer activity for use in this invention includes 2-[(pyridyl)-methylsulfinyl or -methylthio]benzimidazole derivative and a salt thereof, for instance. The preferred compounds are represented by the formula (I) or salts thereof.

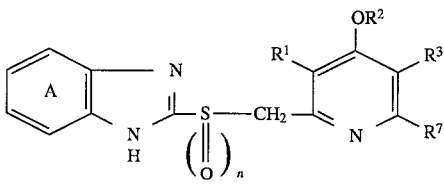

$$\text{(I)}$$

wherein ring A may optionally be substituted, $R^1$, $R^3$ and $R^7$ are, the same or different, hydrogen, an alkyl or alkoxy group, $R^2$ is a hydrocarbon group which may optionally be substituted, and n is 0 or 1.

These compounds are described in, for example, U.S. Pat. No. 4,045,563, U.S. Pat. No. 4,255,431, U.S. Pat. No. 4,359,465, U.S. Pat. No. 4,472,409, U.S. Pat. No. 4,508,905, JP-A-59 181277, U.S. Pat. No. 4,628,098, U.S. Pat. No. 4,738,975, U.S. Pat. No. 5,045,321, U.S. Pat. No. 4,786,505, U.S. Pat. No. 4,853,230, U.S. Pat. No. 4,769,456, U.S. Pat. No. 5,045,552, EP-A-295603, U.S. Pat. No. 5,312,824, EP-A-166287 and EP-A-519365, etc.

Referring to the above formula (I), the substituent that may optionally be present on ring A includes halogen, alkyl which may be substituted, cycloalkyl which may be substituted, alkenyl which may be substituted, alkoxy which may be substituted, cyano, carboxy, carbalkoxy, carbalkoxyalkyl, carbamoyl, carbamoylalkyl, hydroxy, hydroxyalkyl, acyl, carbamoyloxy, nitro, acyloxy, aryl, aryloxy, alkylthio and alkylsulfinyl, among others.

The respective substituent groups are now specifically described.

The halogen may for example be fluorine, chlorine, bromine or iodine. The preferred halogens are fluorine and chlorine. The most advantageous is fluorine.

The alkyl group for the alkyl which may be substituted includes straight-chain or branched alkyl groups of 1 to 10 carbon atoms (e.g. methyl, ethyl, n-propyl, isopropyl, n-butyl, isobutyl, sec-butyl, tert-butyl, n-pentyl, isopentyl, neopentyl, hexyl, heptyl, octyl, nonyl, decyl, etc.). The preferred groups are $C_{1-6}$ straight-chain or branched alkyl groups. The more advantageous are $C_{1-3}$ straight-chain or branched alkyl groups. The substituent on such alkyl includes halogen, nitro, cyano, hydroxy, carboxy, amidino, guanidino, carbamoyl and amino which may be mono- or di-substituted by alkyl, acyl, etc., among others.

The cycloalkyl group for the cycloalkyl which may be substituted includes $C_{3-7}$ cycloalkyl groups. Species of such cycloalkyl are cyclopropyl, cyclobutyl, cyclopentyl, cyclohexyl and cycloheptyl. Such cycloalkyl groups may each be substituted by, for example, halogen, nitro, cyano, hydroxy, carboxy, amidino, guanidino, carbamoyl and amino which may be mono- or di-substituted by alkyl, acyl, etc., among others.

The alkenyl group for the alkenyl which may be substituted includes $C_{2-16}$ straight-chain or branched alkenyl groups, to mention preferred examples. Thus, the alkenyl group specifically includes allyl, vinyl, crotyl, 2-penten-1-yl, 3-penten-1-yl, 2-hexen-1-yl, 3-hexen- 1-yl, 2-methyl-2-propen-1-yl and 3-methyl-2-buten- 1-yl, among others. The preferred groups are $C_{2-6}$ straight-chain or branched alkenyl groups. The more advantageous are $C_{2-4}$ straight-chain or branched alkenyl groups. Such alkenyl groups may have substituents, such as halogen, nitro, cyano, amidino, guanidino and amino which may be mono- or di-substituted by alkyl, acyl, etc., among others. The alkenyl groups mentioned above include isomers (E- and Z-forms) with respect to the double bond.

The alkoxy group for the alkoxy which may be substituted includes $C_{1-10}$ alkoxy groups, among others. As such, the alkoxy group specifically includes methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, octyloxy, nonyloxy, cyclobutoxy, cyclopentoxy, cyclohexyloxy and so on. The preferred are $C_{1-6}$ alkoxy groups. The more advantageous are $C_{1-6}$ alkoxy groups. Such alkoxy groups may be substituted by, for example, halogen, nitro, amidino, quanidio and amino which may be mono- or disubstituted by alkyl, acyl, etc., among others.

The halogen which may occur as a substituent on the alkyl, cycloalkyl, alkenyl or alkoxy group includes chlorine, bromine, fluorine and iodine.

The alkyl moiety of the alkylamino which may substitute the above alkyl, cycloalkyl, alkenyl or alkoxy group includes $C_{1-6}$ straight-chain or branched alkyl groups, among preferred examples. Thus, it specifically includes methyl, ethyl, n-propyl, isopropyl, n-butyl, isobutyl, tert-butyl, sec-butyl, n-pentyl, isopentyl, n-hexyl, isohexyl and so on. Particularly advantageous, among others, are $C_{1-4}$ straight-chain or branched alkyl groups.

The acyl moiety of the acylamino which may substitute the above alkyl, cycloalkyl, alkenyl or alkoxy group includes acyl groups derived from organic carboxylic acids, for instance. The preferred groups are $C_{1-6}$ alkanoyl groups, such as formyl, acetyl, propionyl, butyryl, isobutyryl, valeryl, isovaleryl, pivaloyl, hexanoyl, etc. Particularly desirable are $C_{1-4}$ alkanoyl groups.

The number of substituents on the above alkyl, cycloalkyl, alkenyl or alkoxy group may range from 1 to 6, preferably 1 to 3.

The substituted alkyl group specifically includes trifluoromethyl, trifluoroethyl, difluoromethyl, trichloromethyl, hydroxymethyl, 1-hydroxyethyl, 2-hydroxyethyl, methoxyethyl, ethoxyethyl, 1-methoxyethyl, 2-methoxyethyl, 2,2-dimethoxyethyl, 2,2-diethoxyethyl and 2-diethylphosphorylethyl, among others. The preferred groups are difluoromethyl, trifluoromethyl and hydroxymethyl. The more desirable is trifluoromethyl.

The substituted cycloalkyl group specifically includes 2-aminocyclopropan-1-yl, 4-hydroxycyclopentan- 1-yl and 2,2-difluorocyclopentan-1-yl, among others.

The substituted alkenyl group specifically includes 2,2-dichlorovinyl, 3-hydroxy-2-propen-1-yl, 2-methoxyvinyl and so on.

The substituted alkoxy group specifically includes difluoromethoxy, trifluoromethoxy, 2,2,2-trifluoroethoxy, 2-methoxyethoxy, 4-chlorobenzyloxy, 2-( 3,4-dimethoxyphenyl)ethoxy and so on. The preferred one is difluoromethoxy.

The alkoxy moiety of the carbalkoxy group includes $C_{1-7}$ alkoxy groups (e.g. methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, etc.).

The alkoxy moiety of the carbalkoxyalkyl group includes $C_{1-4}$ alkoxy groups (e.g. methoxy, ethoxy, n-propoxy, isopropoxy, n-butoxy, isobutoxy, sec-butoxy, tert-butoxy, etc.), among others. The alkyl moiety of the carbalkoxyalkyl group includes $C_{1-4}$ alkyl groups (e.g. methyl, ethyl, n-propyl, isopropyl, n-butyl, isobutyl, sec-butyl, tert-butyl, etc.), among others. Specifically, carbomethoxymethyl, 2-carbomethoxyethyl, 2-carbomethoxypropyl, carbethoxymethyl, 2-carbethoxyethyl, 1-carbomethoxypropyl, carbopropoxymethyl, carbobutoxymethyl, etc. can be mentioned.

The alkyl moiety of the carbamoylalkyl group includes $C_{1-4}$ alkyl groups (e.g. methyl, ethyl, n-propyl, isopropyl, n-butyl, isobutyl, sec-butyl, tert-butyl, etc.).

The alkyl moiety of the hydroxyalkyl group includes $C_{1-7}$ alkyl groups (e.g. methyl, ethyl, n-propyl, isopropyl, n-butyl, isobutyl, sec-butyl, tert-butyl, n-pentyl, isopentyl, neopentyl, hexyl, heptyl, etc.)

The acyl group and the acyl moiety of the acyloxy group respectively include $C_{1-4}$ alkanoyl groups such as formyl, acetyl, propionyl, butyryl, isobutyryl and so on.

The aryl group and the aryl moiety of the aryloxy group respectively include $C_{6-12}$ aryl groups (e.g. phenyl, naphthyl, etc.).

The alkyl moiety of the alkylthio or alkylsulfinyl group includes $C_{1-6}$ alkyl groups (e.g. methyl, ethyl, n-propyl, isopropyl, n-butyl, isobutyl, sec-butyl, tert-butyl, n-pentyl, isopentyl, neopentyl, hexyl, etc.)

The number of substituents on substituted ring A is preferably 1 to 4 and, for still better results, 1 to 2. The positions of such substituents on the benzene ring may for example be the 4- and 5-positions. The 5-position is preferred.

The preferred ring is ring A which may optionally be substituted by i) halogen, ii) alkyl group which may be substituted, iii) cycloalkyl group which may be substituted, iv) alkenyl group which may be substituted or v) alkoxy group which may be substituted.

The alkyl group represented by $R^1$, $R^3$ or $R^7$ includes $C_{1-10}$ straight-chain or branched alkyl groups. Among such alkyl groups are methyl, ethyl, n-propyl, isopropyl, n-butyl, isobutyl, sec-butyl, tert-butyl, n-pentyl, isopentyl, neopentyl, hexyl, heptyl, octyl, nonyl, decyl and so on. Among others, $C_{1-6}$ straight-chain or branched alkyl groups are preferred, and $C_{1-3}$ straight-chain or branched alkyl groups are particularly desirable.

The alkoxy group represented by $R^1$, $R^3$ or $R^7$ includes $C_{1-10}$ alkoxy groups. Among such alkoxy groups are methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, octyloxy, nonyloxy, cyclobutoxy, cyclopentoxy, cyclohexyloxy and so on. The preferred groups are $C_{1-6}$ alkoxy groups. The more desirable are $C_{1-3}$ alkoxy groups.

The hydrocarbon moiety of the hydrocarbon group which may optionally be substituted, represented by $R^2$, includes $C_{1-13}$ hydrocarbon group such as $C_{2-6}$ straight-chain or branched alkyl groups (e.g. methyl, ethyl, propyl, isopropyl, butyl, isobutyl, sec-butyl, pentyl, isopentyl, hexyl, etc.), $C_{2-6}$ alkenyl groups (e.g. vinyl, allyl, 2-butenyl, methylallyl, 3-butenyl, 2-pentenyl, 4-pentenyl, 5-hexenyl, etc.), $C_{2-6}$ alkinyl groups (e.g. ethinyl, propargyl, 2-butin-1-yl, 3-butin-2-yl, 1-pentin-3-yl, 3-pentin-1-yl, 4-pentin-2-yl, 3-hexin-1-yl, etc.), $C_{3-6}$ cycloalkyl groups (e.g. cyclopropyl, cyclobutyl, cyclopentyl, cyclohexyl, etc.), $C_{3-6}$ cycloalkenyl groups (e.g. cyclobutenyl, cyclopentenyl, cyclohexenyl, cyclohexadienyl, etc.), and $C_{7-13}$ aralkyl groups (e.g. benzyl, 1-phenethyl, 2-phenethyl, etc.), and $C_{6-10}$ aryl groups (e.g. phenyl, naphthyl, etc.), among others. Among others, $C_{1-6}$ straight-chain or branched alkyl groups (e.g. methyl, ethyl, propyl, isopropyl, butyl, isobutyl, sec-butyl, pentyl, isopentyl, hexyl, etc.) are preferred. Particularly preferred are $C_{1-4}$ straight-chain or branched alkyl groups.

The substituent group of the substituted hydrocarbon group includes, for example, $C_{6-10}$ aryl groups (e.g. phenyl, naphthyl, etc.), amino, $C_{1-6}$ alkylamino (e.g. methylamino, ethylamino, isopropylamino, etc.), di-$C_{1-6}$ alkylamino (e.g. dimethylamino, diethylamino, etc.), N-aralkyl-N-cycloalkylamino (e.g. N-benzyl-N-cyclohexylamino etc.), N-aralkyl-N-alkylamino [e.g. N-(1-naphthylmethyl)-N-ethylamino, etc.], azido, nitro, halogen (e.g. fluorine, chlorine, bromine and iodine), hydroxy, $C_{1-4}$ alkoxy (e.g. methoxy, ethoxy, propoxy, butoxy, etc.), $C_{6-10}$ aryloxy (e.g. phenoxy, naphthyloxy, etc.), $C_{1-6}$ alkylthio (e.g. methylthio, ethylthio, propylthio, etc.), $C_{6-10}$ arylthio (e.g. phenylthio, naphthylthio, etc.), cyano, carbamoyl, carboxy, $C_{1-4}$ alkoxycarbonyl (e.g. methoxycarbonyl, ethoxycarbonyl, etc.), $C_{7-11}$ aryloxycarbonyl (e.g. phenoxycarbonyl, 1-naphthyloxycarbonyl, 2-naphthyloxycarbonyl, etc.), carboxy-$C_{1-4}$ alkoxy (e.g. carboxymethoxy, 2-carboxyethoxy, etc.), $C_{1-6}$ alkanoyl (e.g. formyl, acetyl, propionyl, isopropionyl, butyryl, pentanoyl, hexanoyl, etc.), $C_{7-11}$ aroyl (e.g. benzoyl, 1-naphthoyl, 2-naphthoyl, etc.), $C_{6-10}$ arylsulfonyl (e.g. benzenesulfonyl, 1-naphthylsulfonyl, 2-naphthylsulfonyl, etc.), $C_{1-6}$ alkylsulfinyl (e.g. methylsulfinyl, ethylsulfinyl, etc.), $C_{6-10}$ arylsulfinyl (e.g. benzenesulfinyl, 1-naphthylsulfinyl, 2-naphthylsulfinyl, etc.), $C_{1-6}$ alkylsulfonyl (e.g. methylsulfonyl, ethylsulfonyl, etc.), 5- or 6-membered heterocyclic groups having 1 to 4 hetero-atoms (e.g. N, O, S, etc.) (e.g. 2-furyl, 2-thienyl, 4-thiazolyl, 4-imidazolyl, 4-pyridyl, 1,3,4-thiadiazol-2-yl, 1-methyl- 5-tetrazolyl, etc.), 5- or 6-membered heterocyclic carbonyl groups having 1 to 4 hetero-atoms (e.g. N, O, S) (e.g. 2-furoyl, 2-thenoyl, nicotinoyl, isonicotinyl, etc.) and 5- or 6-membered heterocyclic thio groups having 1 to 4 hetero-atoms (e.g. N, O, S, etc.) (e.g. 4-pyridylthio, 2-pyrimidylthio, 1,3,4-thiadiazol-2-ylthio, 1-methyl-5-tetrazolythio, etc.). The heterocyclic thio groups may each form a bicyclic fused structure with a benzene ring (e.g. 2-benzothiazolylthio, 8-quinolylthio, etc.). The preferred substituents, among them, are halogen (e.g. fluorine, chlorine, bromine and iodine), hydroxy, and $C_{1-4}$ alkoxy (e.g. methoxy, ethoxy, propoxy, butoxy, etc.).

The number of such substituents may range from 1 to 5 and is preferably 1 to 3.

$R^1$ is preferably hydrogen, alkyl groups or alkoxy groups, more preferably, $C_{1-6}$ alkyl group or $C_{1-6}$ alkoxy groups. Particularly, $C_{1-3}$ alkyl groups are preferable.

$R^3$ is preferably hydrogen, alkyl groups or alkoxy groups, more preferably, hydrogen or $C_{1-4}$ alkyl groups. Particularly, hydrogen is preferable.

$R^2$ is preferably $C_{1-6}$ alkyl groups which may optionally be substituted by 1) halogen, 2) hydroxyl or 3) $C_{1-4}$ alkoxy groups, more preferably, $C_{1-4}$ alkyl groups which may optionally be substituted by (1) halogen or (2) $C_{1-4}$ alkoxy groups.

$R^7$ is preferably hydrogen.

n is preferably 1.

The benzimidazole compound for use in this invention includes, among specific examples, 2-[2-[3-methyl-4-(2,2,2-trifluoroethoxy)pyridyl]methylsulfinyl]benzimidazole (lansoprazole), 2-[(2-pyridyl)methylsulfinyl]benzimidazole (thimoprazole), 2-[2-(3,5-dimethyl- 4-methoxypyridyl)methylsulfinyl]-5-methoxy-1H-benzimidazole (omeprazole), sodium salt of 2-[2-[4-(3-methoxypropoxy)- 3-methylpyridyl]methylsulfinyl]-1H-benzimidazole, 2-[2-(3,4-dimethoxypyridyl)methylsulfinyl]- 5-difluoromethoxy-1H-benzimidazole (pantoprazole), 2-[2-[3-methyl-4-(2,2,3,3-tetrafluoropropoxy)pyridyl]methylthio]benzimidazole and so on.

The benzimidazole compound or its salt for use in this invention can be produced by, inter alia, the processes described in the published literature such as Japanese and European laid-open patents and U.S. patents as mentioned hereinbefore, for example, U.S. Pat. No. 4,255,431, U.S. Pat. No. 4,508,905, U.S. Pat. No. 4,628,098, U.S. Pat. No. 4,738,975 and U.S. Pat. No. 5,312,824, or any processes analogous therewith.

The salt of the benzimidazole compound is preferably a physiologically harmless salt. The physiologically harmless salt includes salts with inorganic bases, salts with organic bases, and salts with basic amino acids. Among the inorganic bases mentioned above are alkali metals (e.g. sodium, potassium, etc.) and alkaline earth metals (e.g. calcium, magnesium, etc.). The organic bases may be trimethylamine, triethylamine, pyridine, picoline, N,N-dibenzylethylenediamine, ethanolamine, diethanolamine, trishydroxymethylaminomethane, dicyclohexylamine, etc. The basic amino acids may be arginine, lysine and so on.

These salts can be produced by the per se known production processes, for example the processes described in EP-A-295603 and U.S. Pat. No. 4,738,974 or any processes analogous therewith.

The water-soluble carboxylic acid amide for use in this invention is a compound whose solubility in water is at least about 0.1 w/w %, preferably, a compound whose solubility in water is at least about 1 w/w %. More desirably, the water-soluble carboxylic acid amide is a compound represented by the formula (II):

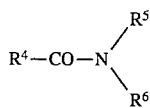

wherein $R^4$ is hydrogen, amino, an alkyl group which may optionally be substituted, an aryl group which may optionally be substituted, or a N-containing heterocyclic group which may optionally be substituted, $R^5$ and $R^6$ are, the same or different, hydrogen or an alkyl group.

The alkyl group which may optionally be substituted, represented by $R^4$, includes the groups mentioned for the substituents on ring A, among others.

The aryl group for the aryl group which may optionally be substituted, represented by $R^4$, includes $C_{6-12}$ aryl groups such as phenyl, naphthyl, etc., for instance.

The heterocyclic group for the heterocyclic group which may optionally be substituted, represented by $R^4$, includes 5- or 6-membered heterocyclic groups having 1 to 4 heteroatoms (e.g. nitrogen, oxygen, sulfur, etc.) as ring members (e.g. 2-pyridyl, 3-pyridyl, pyrimidinyl, pyrazinyl, pyridazinyl, piperazinyl, furyl, thiazolyl, oxazolyl, thienyl, pyrrolyl, furyl, pyranyl, etc.).

The substituents for the substituted aryl or substituted heterocyclic group includes $C_{6-10}$ aryl (e.g. phenyl, naphthyl, etc.), amino, nitro, halogen (e.g. fluorine, chlorine, bromine or iodine), hydroxy, cyano, carboxy and so on.

$R^4$ is preferably hydrogen, amino, $C_{1-8}$ alkyl, phenyl, pyridyl or the like.

The alkyl group represented by $R^5$ or $R^6$ includes those mentioned for $R^1$ or $R^3$.

$R^5$ or $R^6$ is preferably hydrogen or $C_{1-3}$ alkyl group.

As specific examples of the water-soluble carboxylic amide can be mentioned nicotinamide, dimethylacetamide, dimethylformamide, benzoylamide, urea and so on. Nicotinamide is preferable. Such amides can be used alone or in combination.

The pharmaceutical composition of this invention may be liquid or solid. The liquid composition may, for example, be an aqueous solution comprising the benzimidazole compound having antiulcer activity and the water-soluble organic carboxylic acid amide. The solid composition may, for example, be a solid preparation obtainable by freeze-drying or spray-drying the above aqueous solution or a mixture of the benzimidazole compound having antiulcer activity and a water-soluble carboxylic acid amide which is solid at ordinary temperature. The preferred solid preparation is a lyophilizate. The aqueous preparation mentioned above includes an aqueous solution of such solid preparation. Still, the above solid composition may be in the form of a kit wherein the solid preparation and an infusion are formulated into separate preparations.

The technology for producing the pharmaceutical composition of this invention is now described.

An aqueous solution, for instance, can be produced by dissolving the benzimidazole compound having antiulcer activity and water-soluble organic carboxylic acid amide in the per se conventional manner. This aqueous solution is preferably alkaline. The pH of the aqueous solution is preferably about 9–12 and, for still better results, about 9.5–11. The base which can be used for rendering the aqueous solution basic is preferably a strong base, e.g. alkali metal hydroxides such as sodium hydroxide, potassium hydroxide, etc., alkali metal carbonates such as sodium carbonate, potassium carbonate, etc., and arginine, to name but a few examples. Preferred are alkali metal hydroxides.

Where a strong base is thus used, an acid may be added for purposes of buffering the solution. The acid that can be used includes glycine, sodium dihydrogen phosphate, sodium citrate and so on.

The concentration of the benzimidazole compound in aqueous solution may for example be about 2–30 mg/ml, preferably about 5–30 mg/ml. It is just sufficient that this concentration permits successful lyophilization in a subsequent procedure.

Referring to the manufacture of a solid pharmaceutical composition, a lyophilizate, for instance, can be produced by freeze-drying an aqueous solution, preferably an alkaline aqueous solution, which comprises the benzimidazole compound having antiulcer activity and water-soluble carboxylic acid amide in the per se conventional manner. An exemplary procedure comprises freezing the aqueous solution at about $-25°$ C. and, with the internal negative pressure of the freeze-dryer being maintained at about 0.1 Torr or less, increasing the plate temperature at a rate of about $5°–20°$ C./hour to an ultimate temperature of about $25°$ C. $-40°$ C.

Where lyophilization is carried out, a form regulator may be added to an aqueous solution of the benzimidazole compound having antiulcer activity for the purpose of improving the morphology of the lyophilizate. The form regulator mentioned above includes various sugars (e.g. sugar alcohols such as mannitol, xylitol, inositol, sorbitol, etc., hexose-based disaccharides such as maltose, sucrose, lactose, etc., and monosaccharides such as glucose), neutral amino acids (e.g. glycine, alanine, proline, valine, methionine, etc.) and alkali metal salts of succinic acid (e.g. sodium succinate, etc.). Preferred, among these form regulators, are sugars. Particularly, sugar alcohols are preferred.

Where a spray-dried preparation is the objective product, the aqueous solution described above is spray-dried by a per se known technique. An exemplary procedure comprises ejecting the aqueous solution in mist form from a spray dryer nozzle (e.g. a twin nozzle, a pressure nozzle, etc.) or rotary disk into its drying chamber at a flow rate of about 5–20 ml/minute (e.g. drying chamber inlet and out temperatures: about 80°–120° C. and about 30° to 50° C., respectively; air flow rate about 70–100 kg/hour).

The freeze-dried or spray-dried product that can be obtained as above is a white mass or powder which undergoes little change in appearance with time, thus imparting a long shelf-life to the benzimidazole compound.

Where the water-soluble carboxylic acid amide used in this invention is solid at ordinary temperature, it can be directly mixed with the benzimidazole compound having antiulcer activity to provide a composition. The mixing method is not critical and any known procedure can be employed.

Where such a solid pharmaceutical composition is processed into an aqueous solution, it is preferably dissolved or diluted extemporaneously.

Where the pharmaceutical composition of this invention is an aqueous solution, the concentration of the benzimidazole compound having antiulcer activity in the solution is about 0.03 to about 20 mg/ml, preferably about 0.1 to about 15 mg/ml, and for still better results, about 2 to about 10 mg/ml.

The proportion of the water-soluble carboxylic acid amide is about 1 to about 300 mols, preferably about 2 to about 200 mols, and for still better results, about 5 to about 85 mols, per mole of the benzimidazole compound.

For enhancing the solubility and/or stability of the benzimidazole compound or insuring a further increase in drug absorption, a surfactant can be used concomitantly in this invention.

As examples of the surfactant, there can be mentioned nonionic surfactants such as sorbitan fatty acid esters (e.g. sorbitan monopalmitate, sorbitan sesquistearate, etc.), glycerin fatty acid esters [e.g. glyceryl monostearate (self-emulsifying type), etc.], propylene glycol fatty acid esters (e.g. propylene glycol monostearate), polyoxyethylene glycerin fatty acid esters [e.g. polyoxyethylene(15) glyceryl monostearate, etc.], polyethylene glycol fatty acid esters [e.g. polyoxyethylene(10) monostearate, PEG distearate, etc.], polyoxyethylene alkyl ethers [e.g. polyoxyethylene(21) lauryl ether, polyoxyethylene(20) stearyl ether, etc.], polyoxyethylene hydrogenated castor oil [e.g. polyoxyethylene(80) hydrogenated castor oil, HCO 60 and HCO 50 (trade name, Nikko Chemicals Co.), etc.], polyoxyethylene sorbitol beeswax derivatives [e.g. polyoxyethylene(20) sorbitol beeswax etc.], polyoxyethylene lanolin alcohol [e.g. polyoxyethylene(20) lanolin alcohol etc.], polyoxyethylene sorbitol fatty acid esters [e.g. polyoxyethylene(6) sorbitol hexastearate etc.], Pluronic series surfactants [e.g. Pluronic F68 (Polyoxyethylene[160]polyoxypropylene[30]glycol), Pluronic F127 (Polyoxyethylene[196]polyoxypropylene[67]glycol)], etc., anionic surfactants such as alkali metal dodecyl sulfates [e.g. sodium dodecyl sulfate etc.], alkali metal stearates [e.g. sodium stearate], alkali metal palmitates [e.g. sodium palmitate], and liquid surfactants such as Tween 20 and Tween 80 (Astla Powder Co., USA), among others. Among others, a nonionic surfactant is preferred, particularly, pluronic series surfactant is more preferred. These surfactants can be used singly or plurally in a suitable ratio.

The amount of the surfactant(s) based on each mg of the benzimidazole compound is about 0.01–10 mg, preferably about 0.05–5 mg, and for still better results, about 0.1–1 mg.

Moreover, for improving the solubility or stability of the benzimidazole compound, a variety of salts (e.g. salts of organic acids such as sodium citrate, sodium tartrate, sodium benzoate, etc.) and/or stabilizers (e.g. basic inorganic salts such as magnesium carbonate, calcium carbonate, magnesium hydrogen carbonate, calcium hydrogen carbonate, etc.) may be incorporated or added to the composition of this invention. If necessary, an isotonizing agent (e.g. sodium chloride) for osmotic pressure adjustment and/or a soothing or local anesthetic agent (e.g. glucose, sorbitol, mannitol, benzyl alcohol, mepivacaine hydrochloride, xylocaine hydrochloride, etc.) can also be employed.

Furthermore, a preservative and a pH control agent can be added in small amounts as required.

The preservative mentioned above includes parabens such as methyl p-hydroxybenzoate, propyl p-hydroxybenzoates, etc., alcohols such as chlorobutanol, quaternary ammonium salts such as benzalkonium chloride, benzethonium chloride, cetrimide, etc., sorbic acid, chlorhexidines, thimerosal and so on. Preferred, among them, are parabens.

The pH control agent includes various acids, e.g. inorganic acids such as hydrochloric acid, boric acid, phosphoric acid, carbonic acid, hydrogen carbonic acid, etc., organic acids such as mono- or polycarboxylic acids, amino acids, etc., and various bases, e.g. alkali metal hydroxides such as sodium hydroxide, potassium hydroxide, etc. and alkali metal (hydrogen) carbonates such as sodium hydrogen carbonate, sodium carbonate and so on.

These additives can be used alone or in combination and can be added in a proportion of about 0.001–10 mg, preferably about 0.01–5 mg, per milligram of the banzimidazole compound. For enhancing the solubility of such benzimidazole compound having antiulcer activity, appropriate salts such as sodium chloride, magnesium chloride, potassium chloride, etc. can also be added. These salts may be used in a proportion of about 0.1–30 mg, preferably about 1–20 mg, and for still better results, about 1–10 mg.

The pharmaceutical composition of this invention is generally administered orally or parenterally in a dosage form manufactured by formulating such an active ingredient with a pharmacologically acceptable carrier or excipient.

The pharmaceutical composition of this invention can be put to use in the following manner. Taking a solid composition as an example, it can be extemporaneously dissolved in sterile distilled water or an infusion fluid (e.g. physiological saline, glucose infusion, etc.) and used as, for example, an intravenous, subcutaneous, intramuscular or intravenous drip injection or as an ophthalmic solution. Preparation of such an injection is preferably carried out by the per se known aseptic procedure.

The pharmaceutical composition of this invention is of great use in the prevention and therapy of peptic ulcer (e.g. stomach ulcer, duodenal ulcer, anastomotic ulcer, Zollinger-Ellison Syndrome, etc.), gastritis, reflux esophagitis, etc. and in the treatment of postoperative gastrointestinal hemorrhage in mammalian animals (e.g. mouse, rat, rabbit, cat, dog, cattle, horse, goat, sheep, monkey, and man).

The pharmaceutical composition of this invention has a low toxic potential and is, therefore, safely administered to man and domestic animals, either perorally or parenterally.

The dosage of the pharmaceutical composition of this invention is dependent on dosage form, therapeutic regimen, species of active compound and other factors. However, taking an aqueous composition as an example, the daily dose of the benzimidazole compound having antiulcer activity for a male adult human is preferably about 5–300 mg and more desirably about 10–180 mg. The pharmaceutical composition may be administered once or divided into 2 to 3 times a day.

According to this invention, a water-insoluble benzimidazole compound having antiulcer activity can be solubilized and a stable pharmaceutical composition can be provided. The solid pharmaceutical composition of this invention can be extemporaneously dissolved in sterile distilled water or an infusion (e.g. physiological saline, glucose infusion, etc.) and put to use as an injection with great convenience.

The present invention is hereinafter described in more detail by means of the following experimental examples and working examples.

EXPERIMENTAL EXAMPLE 1

The lyophilizate obtained in Example 1, described hereinafter, was dissolved in 5 ml of water for injection. Immediately following dissolution and 4, 8 and 24 hours thereafter, the appearance and content of lansoprazole in the solution (referred to as Content in Table 1) were investigated. The results are presented in Table 1.

TABLE 1

| This invention | Immediately after dissolution | After 4 hours | After 8 hours | After 24 hours |
|---|---|---|---|---|
| Appearance | Colorless, clear | Colorless, clear | Colorless, clear | Colorless, clear |
| Content (%) | 100 | 98.4 | 97.0 | 99.0 |

The pharmaceutical composition of this invention was well sustained in appearance and content up to 24 hours after dissolution, attesting to its excellent stability.

EXPERIMENTAL EXAMPLE 2

The lyophilizate obtained in Examples 4, 5 and 6, described hereinafter, were respectively dissolved in distilled water at a final concentration of 6 mg as lansoprazole/ml to provide preparations, which were designated as Formulations A, B and C, respectively. On the other hand, 3 g of lansoprazole was dissolved in 115 ml of a 1N-aqueous solution of sodium hydroxide, followed by addition of sufficient distilled water to make 200 ml. This solution was subjected to filtration through a bacterial filter and the filtrate was filled in vials and lyophilized in the conventional manner. The lyophilizate was dissolved in distilled water at a final concentration of 6 mg as lansoprazole/ml to provide a preparation now designated as Formulation D.

Formulations A, B, C and D were compared with one another in regard of color and clarity. The results are shown in Table 2.

TABLE 2

| | Immediately after dissolution | 4 Hours after dissolution | 8 Hours after dissolution | 24 Hours after dissolution |
|---|---|---|---|---|
| This invention | | | | |
| Formulation A | Colorless, clear | Colorless, clear | Colorless, clear | Colorless, clear |
| Formulation B | Colorless, clear | Colorless, clear | Colorless, clear | Colorless, clear |
| Formulation C | Colorless, clear | Colorless, clear | Colorless, clear | Colorless, clear |
| Control Formulation D | Colorless, clear | Micro-fine insoluble matter found | Slight precipitation found | Precipitation and turbidity found |

The contents of lansoprazole of each of Formulations A, B and C were investigated at 24 hours after dissolution. As 100% at immediately after dissolution, each of the contents was at least 96%.

Formulations A, B and C of this invention remained fully acceptable in both appearance and content up to at least 24 hours after dissolution, indicating that the stability of the active substance in each preparation was quite satisfactory.

EXAMPLE 1

In water for injection were dissolved 375 mg of glycine, 12.5 g of nicotinamide and 300 mg of sodium hydroxide followed by addition and dissolution of 1,000 mg of lansoprazole and 1.5 g of mannitol to make a total of 50 ml. This solution was sterilized by filtration and the filtrate was distributed in 1.5 ml portions into 9 cm$^3$ vials and freeze-dried in the routine manner to provide a lyophilizate containing lansoprazole.

EXAMPLE 2

1,000 mg of lansoprazole, 300 mg of methylglucamine and 15 g of nicotinamide were mixed and dissolved in water for injection. The solution was adjusted to pH 10.5 with 1N-aqueous solution of sodium hydroxide to make 50 ml. This solution was sterilized by filtration and the filtrate was spray-dried to provide a spray-dried preparation containing lansoprazole.

EXAMPLE 3

3,000 mg of lansoprazole was mixed with 60 g of dimethylacetamide and the mixture was dissolved in water for injection. The solution was adjusted to pH 10.7 and made up to 500 ml with 1N-aqueous solution of sodium hydroxide. This solution was sterilized by filtration and the filtrate was distributed in 5 ml portions into 10 cm$^3$ vials to provide an aqueous preparation containing lansoprazole.

EXAMPLE 4

3,000 mg of lansoprazole, 18 g of nicotinamide and 1 g of Pluronic F68 were blended in powdery form and, then, dissolved in 115 ml of 0.1N-aqueous solution of sodium hydroxide to make 200 ml. This solution was filtered through a bacterial filter and the filtrate was distributed in 2 ml portions into 17 cm$^3$ vials and lyophilized in the conventional manner to provide a pharmaceutical preparation containing lansoprazole.

EXAMPLE 5

3,000 mg of lansoprazole and 9 g of nicotinamide were blended in powdery form and dissolved in 115 ml of 0.1N-aqueous solution of sodium hydroxide to make 200 ml. This solution was filtered through a bacterial filter and the filtrate was distributed in 2 ml portions into 17 cm$^3$ vials and lyophilized in the conventional manner to provide a pharmaceutical preparation containing lansoprazole.

EXAMPLE 6

3,000 mg of lansoprazole was dissolved in 40 ml of 1N-aqueous solution of sodium hydroxide. To this solution were added 9 g of nicotinamide, 0.5 g of Pluronic F68, 1.1 g of citric acid, 5 g of disodium hydrogenphosphate, 1.2 g of sodium hydrogen carbonate and 7 g of mannitol. The mixture was diluted with sufficient distilled water to make 300 ml. This solution was filtered through a bacterial filter and the filtrate was distributed in 3 ml portions into 17 cm$^3$ vials and lyophilized in the conventional manner to provide a pharmaceutical preparation containing lansoprazole.

What we claim is:

1. A pharmaceutical composition which comprises a benzimidazole compound having anti-ulcer activity and a water-soluble carboxylic acid amide represented by the formula:

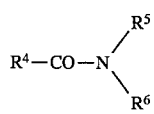

wherein $R^4$ is a nitrogen-containing heterocyclic group which may optionally be substituted, $R^5$ and $R^6$, which are the same or different, are hydrogen or an alkyl group.

2. The composition as claimed in claim 1, wherein the benzimidazole compound is represented by the formula:

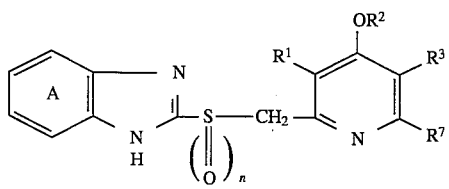

wherein ring A may optionally be substituted; $R^1$, $R^3$, and $R^7$, which are the same or different, are hydrogen, an alkyl group or an alkoxy group; $R^2$ is a hydrocarbon group which may optionally be substituted; and n is 0 or 1; or a salt thereof.

3. The composition as claimed in claim 2, wherein $R^1$ and $R^3$, which are the same or different, are hydrogen, an alkyl group or an alkoxy group, $R^2$ is a $C_{1-4}$ alkyl group which may optionally be substituted by a halogen or a $C_{1-4}$ alkoxy group, and $R^7$ is a hydrogen atom.

4. The composition as claimed in claim 1, wherein the benzimidazole compound is 2-[2-[3-methyl-4-(2,2,2-trifluoroethoxy)pyridyl]methylsulfinyl]benzimidazole.

5. The composition as claimed in claim 1, wherein the water-soluble carboxylic acid amide is nicotinamide.

6. The composition as claimed in claim 1, which further comprises at least one sugar.

7. The composition as claimed in claim 6, wherein the sugar is a sugar alcohol.

8. The composition as claimed in claim 1, which is a lyophilizate.

9. The composition as claimed in claim 1, which is an aqueous solution.

10. The composition as claimed in claim 9, wherein the aqueous solution is an injectable solution.

* * * * *